United States Patent [19]

Walker et al.

[11] 4,428,782
[45] Jan. 31, 1984

[54] PRODUCTION OF ALUMINIUM ALLOY STRIP

[75] Inventors: David J. Walker, South Wirral; Kenneth Amor, Higher Bebington, both of England

[73] Assignee: The Electricity Council, London, Great Britain

[21] Appl. No.: 401,155

[22] Filed: Jul. 23, 1982

[51] Int. Cl.³ .................... C21D 1/54; C21D 11/00
[52] U.S. Cl. ................................. 148/129; 148/128; 266/87; 266/90
[58] Field of Search .............. 148/129, 128, 159, 415; 266/78, 79, 90, 104, 87; 219/10.77; 374/163, 166, 167; 324/62 R, 65 R, 65 P

[56] References Cited

U.S. PATENT DOCUMENTS

| | | | |
|---|---|---|---|
| 1,386,645 | 8/1921 | Moore | 148/128 |
| 3,058,840 | 10/1962 | Kerr et al. | 266/104 |
| 3,310,736 | 3/1967 | Bayly et al. | 324/65 P |
| 4,000,458 | 12/1976 | Miller et al. | 324/62 |

FOREIGN PATENT DOCUMENTS 2612153 10/1976 Fed. Rep. of Germany ...... 266/104
2091456 7/1982 United Kingdom .

OTHER PUBLICATIONS

Schröder et al., "Measurement of the Surface Temperature of Cold Rolled Steel"; Testing of Matts. and Components by Infrared Radiation, pp. 129-137, 11/18/75.

Primary Examiner—L. Dewayne Rutledge
Assistant Examiner—S. Kastler
Attorney, Agent, or Firm—Beveridge, DeGrandi and Kline

[57] ABSTRACT

In the heat treatment of aluminium alloy strip, in which hardening of the material is effected by heat treatment to dissolve pre-existing precipitates in the metal matrix followed by quenching and ageing, the electrical conductance of the strip after quenching is measured using a conductivity probe scanned across the width of the strip, the heating being controlled in accordance with the measured conductance so as to obtain uniform electrical conductance across the width of the strip. This measured electrical conductance has a close correlation with the required mechanical properties. A transmitter producing an electromagnetic field is moved across the strip and a receiver, picking up signals due to the eddy currents in the strip, provides an output automatically controlling the movement of flux modifiers of a transverse flux induction heater to control the strip heating.

14 Claims, 4 Drawing Figures

PRODUCTION OF ALUMINIUM ALLOY STRIP

BACKGROUND OF THE INVENTION

1. Field of the Invention

This invention relates to the production of aluminium alloy in strip form.

2. Prior Art

In a continuous process line for producing an aluminium alloy in strip form, cold rolling is often used to obtain a strip with accurate dimensions and a good surface. Cold rolling leaves the material in a work-hardened state in which it tends to be strong but not very ductile. To restore the ductility, the strip is annealed by maintaining it for a suitable time at a temperature in the range of 200°–450° C. Another method of obtaining high strengths in aluminium alloy strip is precipitation hardening. This precipitation hardening treatment hardens the strip by causing an extremely fine precipitate dispersion to form in the matrix. The heat treatment required to produce this dispersion consists of solution treatment in which any pre-existing precipitates are dissolved to give a uniform solid solution, the heat treatment being followed by rapid quenching of the material to room temperature so as to retain the solid solution. The quenching is followed by ageing, which can take place at room temperature and/or temperatures in the range of 100° to 200° C. during which the solid solution breaks down to give the fine precipitate dispersion.

On a continuous heat treatment line, there is a possibility of temperature variations across the width of the strip. In some aluminium alloys where the solution treatment is a sensitive function of the solution treatment time and temperature, such temperature variations across the width of the strip can lead to differential solution treatment across the strip width.

It is known to measure the thermal profile across the width of the strip by a scanning system sensitive to the radiation from the strip.

However radiation sensitive scanning systems have been found to be very sensitive to the emissivity of the surface being scanned. With some alloys, which usually are the same alloys as are very sensitive to the solution treatment conditions, the emissivity changes at high temperatures. This change in emissivity masks the true thermal profile of the strip as detected by radiation sensitive scanning systems.

SUMMARY OF THE INVENTION

We have found that the electrical conductance of the strip, as quenched, has a close correlation with the final mechanical properties which it is required to achieve.

According to one aspect of the present invention, in the method of producing aluminium alloy strip in which hardening of the material is effected by heat treatment to dissolve pre-existing precipitates in the metal matrix so as to give a uniform solid solution followed by quenching in a quenching bath and subsequent ageing, the electrical conductance of the strip after quenching is measured using a conductivity probe scanned across the width of the strip or an array of probes across the width of the strip and the degree of heating across the width of the strip is controlled in accordance with the measured conductance so as to tend to obtain uniform electrical conductance across the width of the strip. Preferably the heat treatment is effected using a transverse flux induction heater having adjustable means for controlling the degree of heating across the width of the strip.

The electrical conductance may be measured by means of a non-contacting conductance probe which is repetitively scanned across the strip or an array of probes may be used to determine the conductance profile across the width of the strip. The conductance profile is determined after quenching and preferably automatic control means are provided for controlling the heater to give the required heating power distribution across the width of the strip.

A transverse flux induction heater for the above-described process may comprise a plurality of windings and cores distributed across the width and along the length of the strip. Control of the heating power distribution may be effected by altering the power to individual windings, e.g. by adjusting the air gap, through which the strip passes, or by moving portions of the magnetic cores relative to the windings.

According to another aspect of the invention, heat treatment means for use in a strip mill for producing aluminium alloy strip comprise heating means for heating the strip to a temperature to effect solution treatment in which pre-existing precipitates are dissolved in the metal matrix to give a uniform solid solution, means for quenching the strip after heating so as to retain the solid solution, electrical conductance measuring means arranged to measure the electrical conductance of the strip after quenching either by scanning across the width of the strip or by utilising an array of probes to determine conductance profile and means for differentially adjusting the heating effect across the width of the strip in accordance with the measured conductance profile so as to tend to maintain a uniform conductance across the width of the strip.

The heating means are conveniently transverse flux induction heating means comprising a plurality of windings and cores. The means for differentially adjusting the heating effect conveniently comprises means for altering the air gaps through which the strip passes, between cores on opposite sides of the strip thereby differentially to change the flux distribution across the width of the strip arising from current through windings on the cores. Alternatively the electrical power supplied to said coils may be differentially adjusted to effect the required heating distribution.

The invention furthermore includes within its scope a strip mill incorporating heat treatment means as described above.

DESCRIPTION OF THE PREFERRED EMBODIMENT

Figure 1:
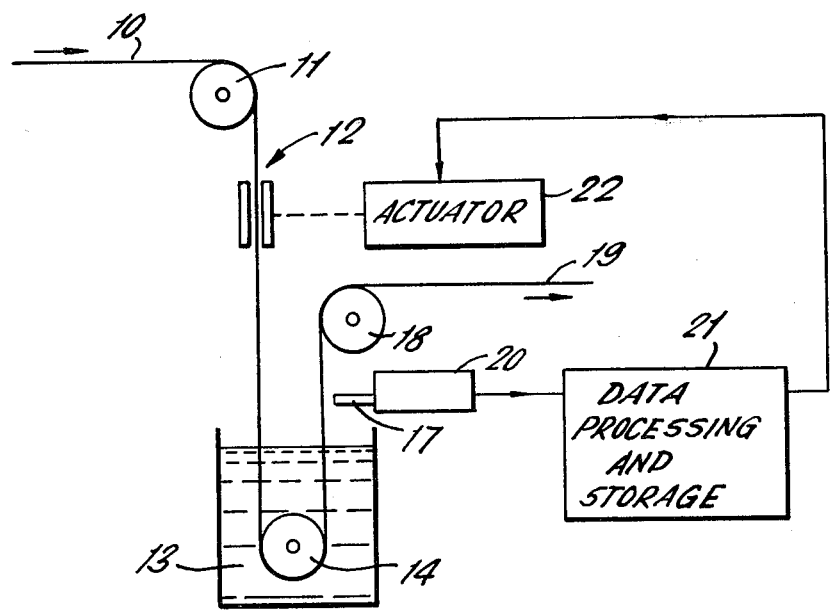
FIG. 1 is a diagrammatic side elevation of part of an apparatus for processing aluminium alloy strip forming one embodiment of the invention.

Referring to FIG. 1 an aluminium alloy strip 10, which is to be heat treated in a continuous process plant, passes over a roller 11 and thence vertically downwards through a transverse flux induction heater 12 to a quenching bath 13 in which it passes around a roller 14 to leave the bath upwardly at 16. Here the electrical conductance of the strip is measured by a scanning probe 17. The strip then passes over a roller 18 and is fed out at 19 for ageing at room temperature, inspection and winding into a roll for subsequent transport and use.

The present invention is concerned more particularly with the control of the heating by the transverse flux induction heater 12. In a continuous heat treatment line using a transverse flux inductor, unless the heating is controlled, there is a possibility of temperature variations across the width of the strip. In some aluminium alloys, where the degree of solution treatment is sensitive to the solution treatment time and temperature, such temperature variations across the width can lead to differential solution treatment across the width. In the apparatus of the present invention, the electrical conductance of the strip is measured across the width of the strip after the quenching operation by a scanning probe 17. This is a non-contacting electrical conductivity measuring device which is mechanically repetitively scanned across the width of the strip by scanning means 20 to provide output information to a data processor storage device 21 which stores information representative of the conductance or conductance variations across the width of the strip. The conductivity measurement will be described later in further detail with reference to FIGS. 3 and 4.

Figure 2:
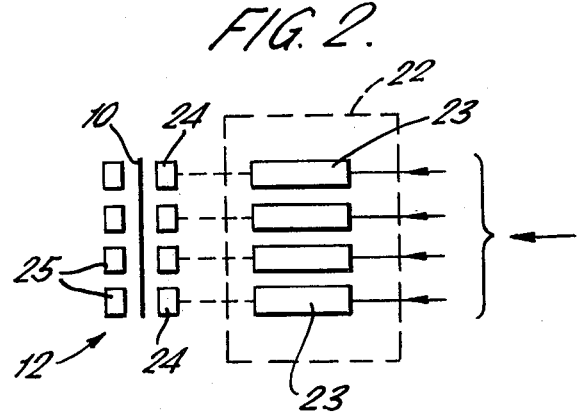
FIG. 2 is a diagrammatic transverse section through the strip and induction heater for explaining the form of heating control employed in the apparatus of FIG. 1.

The data processor 21 provides output control signals for actuator means 22 which adjusts the heating across the width of the strip by the transverse flux induction heater 12. As shown diagrammatically in FIG. 2, the control means 22 may comprise a plurality of actuators 23 which act respectively on individual core and coil units 24 of the transverse induction heater 12. This induction heater comprises core and coil assemblies 24 adjacent one face of the strip and co-operating cores 25 on the opposite face. By moving the assemblies 24 towards and away from their respective co-operating cores 25, the air gap between the cores in each pair may be altered differentially and hence the heating effect may be adjusted differentially across the width of the strip 10. The actuators 23 are controlled by the data processor 21 in such a manner as to tend to maintain a uniform conductance across the width of the strip.

Figure 3:
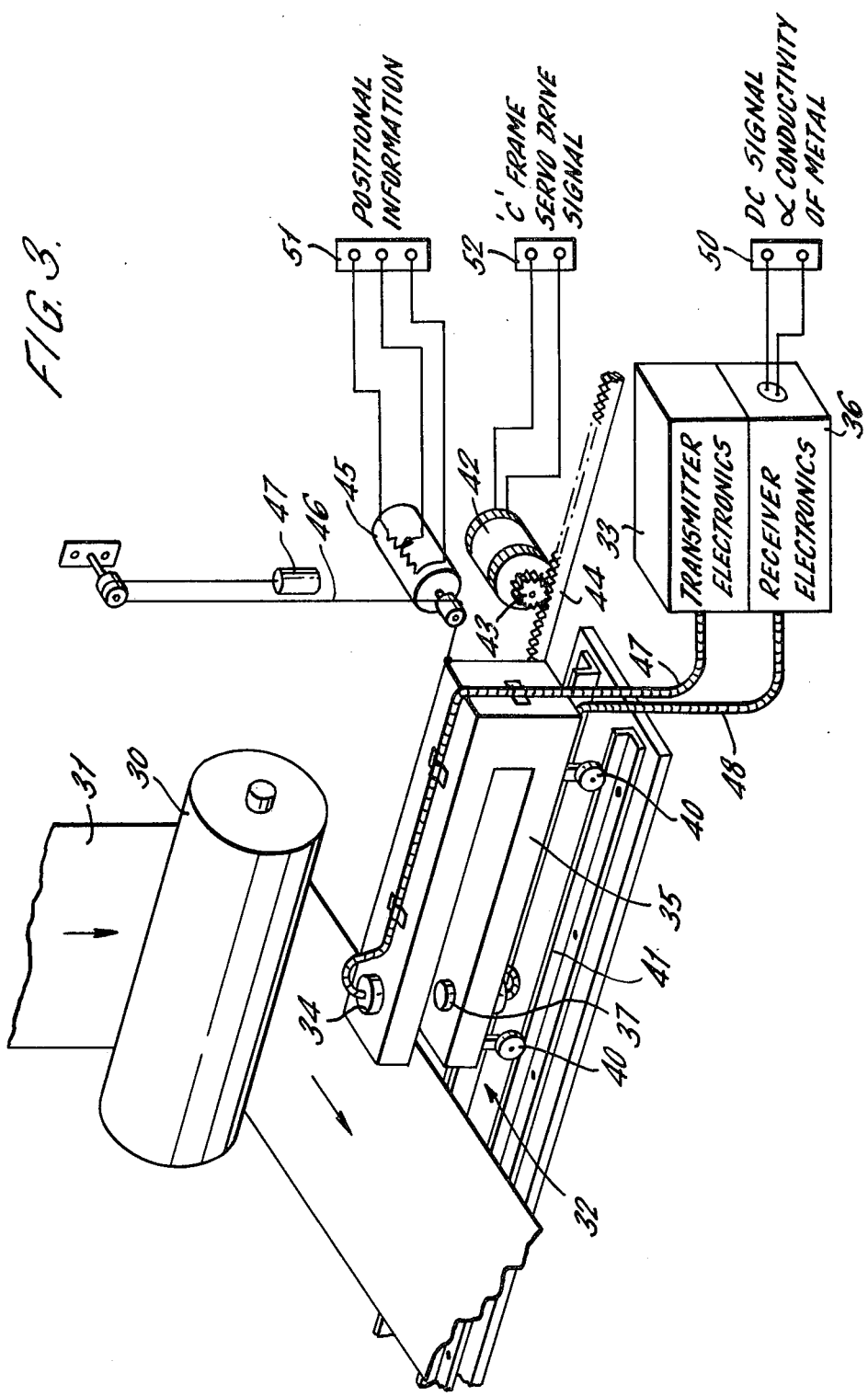
FIG. 3 is a diagram illustrating a conductivity sensing assembly used in the apparatus of FIG. 1.
Figure 4:
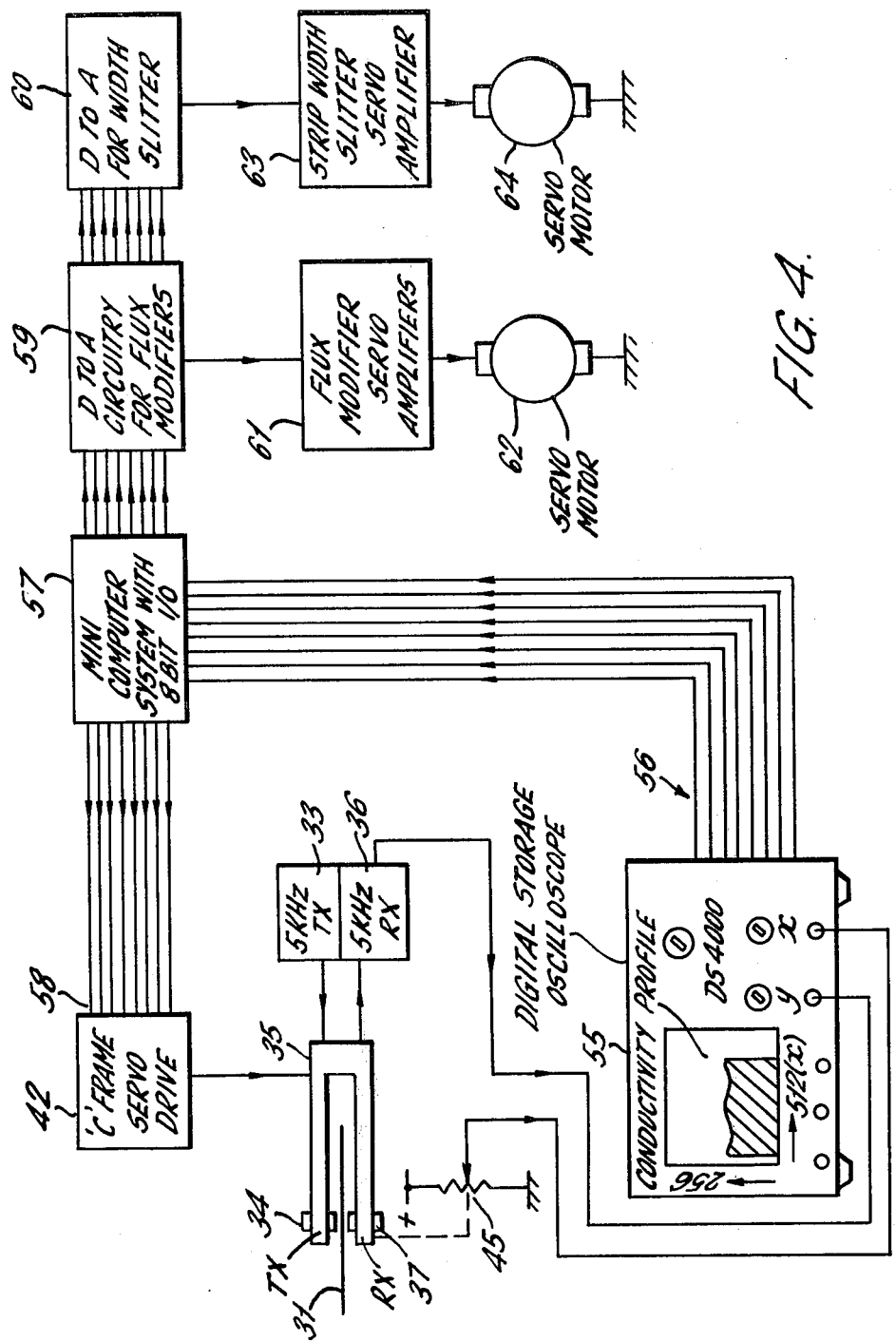
FIG. 4 shows diagramatically the apparatus processing the output of the conductivity sensor of FIG. 3.

FIGS. 3 and 4 illustrate further details of the conductivity measuring apparatus. In FIG. 3, there is shown a roller 30 over which the strip 31 passes, together with a conductivity measurement device 32 situated close to the roller. This device comprises a transmitter 33 with a transmitting head 34 producing an electromagnetic field at a frequency of about 5 kHz, the head being mounted on a C-shaped frame 35 so as to be about 25 mm above the upper surface of the strip 31. Typically the transmitter has a ferrite core driven from a medium power square wave oscillator running at the required frequency, e.g. 5 kHz. The transmitter has a high Q tuned circuit so that the output has a substantially sinusoidal waveform. This field from the transmitter induces eddy currents in the strip 31. A receiver 36 has a receiving head 37 mounted on the frame 35 below the strip, typically about 25 mm away from the strip surface. The receiver has a ferrite head which picks up the signals from the strip and amplifies them.

Changes in the amplitude of the output of the receiver will be due either to gauge variation in the strip or due to conductivity changes. The gauge can be measured automatically a gauge signal employed in processing the information from the receiver if this should be necessary.

The C-shaped frame 35 is mounted on rollers 40 running on rails 41 for movement to and fro across the width of the strip 31, the frame being driven by a servo drive motor 42 through a pinion 43 and rack 44. A signal representative of the transverse position of the transmitter/receiver is obtained from an electrically linear potentiometer 45 which mechanically is constructed as a helical potentiometer driven by a steel wire 46 attached to the frame 35 and tensioned by a counterweight 47.

The transmitter 33 is connected to its head 34 by a flexible cable 47. The receiver 36 is connected to the receiver head 37 by a second flexible cable 48. Output information from the receiver is produced at terminals 50 and output positional information from the potentiometer 45 at terminals 51. The input drive signals for the servo motor are applied at terminals 52.

Referring to FIG. 4, the positional signals and receiver output signals are applied to a digital storage oscilloscope 55 to give a conductivity profile across the width of the strip. The information is in digital form and consists of 512 bytes of information representing the extent of the x-axis (that is the transverse position) and the amplitude for each of these 512 segments is digitised information representative of the appropriate one of 256 conductivity levels.

If the frame 35 is scanned beyond the edges of the strip 31, the resultant large changes in the receiver output gives indications enabling the actual width of the strip to be determined. When the strip line is running normally, cracks, flaws, etc. can be detected on the oscilloscope and appropriate action taken.

The digital output from the oscilloscope 55 is clocked, via an 8-bit data bus 56, into a minicomputer 57. The minicomputer processes the digital information and, via a bus 58 feeds control signals to terminals 52 of the motor 42. The minicomputer also provides digital inputs to first and second digital-to-analogue converters 59, 60. The first digital-to-analogue converter 59 provides instructions, via flux modifier servo amplifiers 61, to a servo motor system 62 for effecting the necessary movements required by the flux modifiers of the transverse flux induction heater. These movements are determined from the conductivity profile by periodic examination of that profile. The second digital-to-analogue converter 60 feeds signals to a strip width slitter servo amplifier 63 controlling a servo motor 64.

Instead of mechanically scanning the conductance probe as described above, it would alternatively be possible to use a plurality of probes spaced apart across the width of the strip to provide, in the data processor, the required information representing the conductance profile (or variations in the conductance) across the strip.

With the above-described form of apparatus, the aluminium strip passes through the transverse flux induction heater 12 (FIG. 1) down into the quenching bath 13. The conductance measurement across the width of the strip as the strip comes out of the quenching bath gives indications which are representative of any unevenness of heating across the width of the strip such as would give non-uniform solution treatment. The control of the heating therefore serves to maintain a more uniform treatment. The measurement of the electrical conductance avoids the problems which occur in attempting more directly to measure the thermal profile across the strip as it leaves the induction heater in that non-contacting temperature sensors are dependent on the emissivity of the surface of the strip and it is known that emissivity of some aluminium alloys changes at high temperatures.

Although one form of heating control has been described in which coil and core assemblies are moved, other forms of control of the heating may be employed, for example by electrical control of the power to the various coils of the inductor.

A further advantage of the above-described device is that it also operates to maintain more uniform heat treatment along the length of the strip.

We claim:

1. A method of producing aluminium alloy strip in which hardening of the material is effected by heat treatment to dissolve pre-existing precipitates in the metal matrix so as to give a uniform solid solution followed by quenching in a quenching bath and subsequent ageing, wherein the electrical conductance of the strip after quenching is measured using a conductivity probe scanned across the width of the strip or an array of probes across the width of the strip and wherein the degree of heating across the width of the strip is controlled in accordance with the measured conductance so as to tend to obtain uniform electrical conductance across the width of the strip.

2. A method as claimed in claim 1 wherein the heat treatment is effected using induction heating.

3. A method as claimed in claim 2 wherein the heat treatment is effected using a transverse flux induction heater having adjustable means for controlling the degree of heating across the width of the strip.

4. A method as claimed in claim 1 wherein the electrical conductance is measured by means of a non-contacting conductance probe which is repetitively scanned across the strip.

5. A method as claimed in claim 1 wherein an array of probes are used to determine the conductance profile across the width of the strip.

6. A method as claimed in claim 1 wherein automatic control means are provided for controlling the heating means to give the required heating power distribution across the width of the strip.

7. A method as claimed in claim 1 wherein the heat treatment is effected by passing the strip through an induction heater having a plurality of windings and wherein the heating power distribution is controlled by altering the power to individual windings of the induction heater.

8. A method as claimed in claim 1 wherein the heat treatment is effected by passing the strip through an air gap in an induction heater between individual core elements carrying windings on one face of the strip and co-operating core elements on the other face of the strip and wherein the heating power distribution is controlled by adjusting the air gap.

9. Heat treatment means for use in a strip mill for producing aluminium alloy strip wherein there are provided heating means for heating the strip to a temperature to effect solution treatment in which pre-existing precipitates are dissolved in the metal matrix to give a uniform solid solution means for quenching the strip after heating so as to retain the solid solution, electrical conductance measuring means arranged to measure the electrical conductance of the strip after quenching either by scanning across the width of the strip or by utilising an array of probes to determine conductance profile and means for differentially adjusting the heating effect across the width of the strip in accordance with the measured conductance profile so as to tend to maintain a uniform conductance across the width of the strip.

10. Heat treatment means as claimed in claim 9 wherein the heating means comprise an induction heater.

11. Heat treatment means as claimed in claim 9 wherein the heating means comprise transverse flux induction heating means having a plurality of windings and cores.

12. Heat treatment means as claimed in claim 11 wherein the means for adjusting the heating effect comprises means for differentially altering the air gaps, through which the strip passes, between cores on opposite sides of the strip of a transverse flux induction heater having a plurality of ferromagnetic cores spaced across the width of the strip on each face thereof thereby to change the flux distribution across the width of the strip arising from current through windings on the cores.

13. Heat treatment means as claimed in claim 11 wherein the means for adjusting the heating effect comprises means for differentially adjusting the electrical power supplied to said coils.

14. A strip mill incorporating heat treatment means as claimed in claim 9.

* * * * *